(12) United States Patent
Stroot (10) Patent No.: US 12,031,992 B2
(45) Date of Patent: Jul. 9, 2024

(54) METHODS AND SYSTEMS FOR CONTROLLING OXIDATIVE STRESS

(71) Applicant: Western Autotroph Company LLC, Liberty Lake, WA (US)

(72) Inventor: Peter Stroot, Liberty Lake, WA (US)

(73) Assignee: Western Autotroph Company LLC, Liberty Lake, WA (US)

( * ) Notice: Subject to any disclaimer, the term of this patent is extended or adjusted under 35 U.S.C. 154(b) by 291 days.

(21) Appl. No.: 17/227,115

(22) Filed: Apr. 9, 2021

(65) Prior Publication Data
US 2021/0333294 A1 Oct. 28, 2021

Related U.S. Application Data (63) Continuation of application No. 16/002,953, filed on Jun. 7, 2018, now Pat. No. 10,976,327, which is a
(Continued)

(51) Int. Cl.
*G01N 33/84* (2006.01)
*G01N 21/64* (2006.01)
*G01N 21/78* (2006.01)

(52) U.S. Cl.
CPC ..... *G01N 33/84* (2013.01); *G01N 2021/6439* (2013.01); *G01N 21/78* (2013.01); *G01N 2800/7009* (2013.01)

(58) Field of Classification Search
CPC ............ G01N 33/84; G01N 21/78; G01N 2021/6439; G01N 2800/7009
See application file for complete search history.

(56) References Cited

U.S. PATENT DOCUMENTS 2,064,529 A 12/1936 Fischer et al.
2,850,449 A 9/1958 Torpey
(Continued)

FOREIGN PATENT DOCUMENTS

WO WO 2008/016631 A 2/2008
WO WO 2010/017338 A1 2/2010
WO WO 2014/004791 1/2014

OTHER PUBLICATIONS

U.S. Appl. No. 14/929,124, filed Oct. 30, 2015, Methods and Systems for Controlling Oxidative Stress in Humans and Animals.
(Continued)

*Primary Examiner* — Brian J. Sines
(74) *Attorney, Agent, or Firm* — Knobbe, Martens, Olson & Bear, LLP (57) ABSTRACT

The present application describes methods and systems for measuring and controlling oxidative stress in animals and humans. The degree of oxidative stress can be measured directly by inducing all of the blood cells to produce excessive reactive oxygen species (ROS) by exposure to an elevated concentration sulfide or other ROS inducing chemical and measuring the fluorescence intensity of a fluorescent dye or color intensity of dye that reacts with ROS. Oxidative stress can be reduced by reducing dietary sulfur, consumption of a methanogenic probiotic, or apheresis methods to replace ROS-positive blood cells with normal blood cells. Plasma oxidative stress can be compared in venous and arterial blood samples to evaluate small vessel disease. Oxidative stress can be increased by increasing dietary sulfur or the use of an intravenous method that exposes blood cells to an elevated blood concentration of sulfide or other ROS inducing chemical.

10 Claims, 3 Drawing Sheets

Related U.S. Application Data continuation of application No. 14/929,124, filed on Oct. 30, 2015, now Pat. No. 9,995,758.

(60) Provisional application No. 62/073,876, filed on Oct. 31, 2014.

(56) References Cited

U.S. PATENT DOCUMENTS

| | | | |
|---|---|---|---|
| 3,220,945 A | 11/1965 | Torpey | |
| 3,241,897 A | 3/1966 | Hollerith, Jr. | |
| 3,386,910 A | 6/1968 | Forrest | |
| RE26,514 E | 12/1968 | Alberston et al. | |
| 3,440,165 A | 4/1969 | Davis et al. | |
| 3,787,316 A | 1/1974 | Brink et al. | |
| 3,859,215 A | 1/1975 | Milne | |
| 3,953,326 A | 4/1976 | Reimann | |
| 3,994,802 A | 11/1976 | Casey et al. | |
| 4,017,402 A | 4/1977 | Fitch | |
| 4,213,857 A | 7/1980 | Ishida et al. | |
| 4,277,342 A | 7/1981 | Hayes et al. | |
| 4,289,625 A | 9/1981 | Tarman et al. | |
| 4,315,823 A | 2/1982 | Witt et al. | |
| 4,551,243 A | 11/1985 | Martin | |
| 4,735,724 A | 4/1988 | Chynoweth et al. | |
| 4,818,407 A | 4/1989 | Bogusch | |
| 4,867,883 A | 9/1989 | Daigger et al. | |
| 4,975,195 A | 12/1990 | Urbani | |
| 4,988,442 A | 1/1991 | Highsmith et al. | |
| 5,019,266 A | 5/1991 | Soeder et al. | |
| 5,076,927 A | 12/1991 | Hunter | |
| 5,173,187 A | 12/1992 | Nader et al. | |
| H1149 H | 3/1993 | Wyman et al. | |
| 5,207,911 A | 5/1993 | Pellegrin et al. | |
| 5,264,349 A | 11/1993 | De Baere | |
| 5,338,445 A | 8/1994 | Zumbragel et al. | |
| 5,429,797 A | 7/1995 | Camiener | |
| 5,439,667 A | 8/1995 | Camiener | |
| 5,451,319 A | 9/1995 | Kobayashi | |
| 5,514,264 A | 5/1996 | Shane | |
| 5,650,069 A | 7/1997 | Hong et al. | |
| 5,651,892 A | 7/1997 | Pollock | |
| 5,656,059 A | 8/1997 | Monster et al. | |
| 5,712,095 A | 1/1998 | Britschgi et al. | |
| 5,723,048 A | 3/1998 | Kobayashi et al. | |
| 5,726,021 A | 3/1998 | Britschgi et al. | |
| 5,733,456 A | 3/1998 | Okey et al. | |
| 5,733,758 A | 3/1998 | Nguyen | |
| 5,770,373 A | 6/1998 | Britschgi et al. | |
| 5,798,043 A | 8/1998 | Khydenko | |
| 5,849,192 A | 12/1998 | Jagush et al. | |
| 5,863,435 A | 1/1999 | Heijnen et al. | |
| 6,077,430 A | 6/2000 | Chudoba et al. | |
| 6,159,371 A | 12/2000 | Dufay | |
| 6,163,932 A | 12/2000 | Rosen | |
| 6,203,683 B1 | 3/2001 | Austin et al. | |
| 6,254,775 B1 | 7/2001 | McElvaney | |
| 6,299,774 B1 | 10/2001 | Ainsworth et al. | |
| 6,372,137 B1 | 4/2002 | Bounds | |
| 6,444,124 B1 | 9/2002 | Onyeche et al. | |
| 6,491,061 B1 | 12/2002 | Lopez et al. | |
| 6,569,334 B1 | 5/2003 | Yoneda | |
| 6,692,642 B2 | 2/2004 | Josse et al. | |
| 6,699,670 B2 | 3/2004 | Rothman et al. | |
| 6,808,879 B1 | 10/2004 | Guillot et al. | |
| 6,861,236 B2 | 3/2005 | Moll et al. | |
| 6,893,567 B1 | 5/2005 | Vanotti et al. | |
| 7,001,519 B2 | 2/2006 | Linden et al. | |
| 7,005,257 B1 | 2/2006 | Haas et al. | |
| 7,011,757 B1 | 3/2006 | Reid | |
| 7,014,763 B2 | 3/2006 | Johnson et al. | |
| 7,195,712 B2 | 3/2007 | Park et al. | |
| 7,641,796 B2 | 1/2010 | Stroot et al. | |
| 7,655,143 B2 | 2/2010 | Stroot et al. | |
| 7,682,823 B1 | 3/2010 | Runyon | |
| 7,683,823 B2 | 3/2010 | Runyon | |
| 7,771,941 B2 | 8/2010 | Stroot et al. | |
| 7,947,440 B2 | 5/2011 | Stroot et al. | |
| 8,110,395 B2 | 2/2012 | Lewnard et al. | |
| 8,535,534 B2 | 7/2013 | Stroot | |
| 8,545,700 B1 | 10/2013 | Stroot et al. | |
| 8,628,666 B2 | 1/2014 | Stroot | |
| 8,795,498 B2 | 8/2014 | Toomey et al. | |
| 8,940,159 B1 | 1/2015 | Stroot et al. | |
| 9,995,758 B1 * | 6/2018 | Stroot | G01N 33/84 |
| 10,976,327 B1 * | 4/2021 | Stroot | G01N 33/84 |
| 2001/0045359 A1 | 11/2001 | Cheng et al. | |
| 2003/0098277 A1 | 5/2003 | Khudenko | |
| 2003/0148379 A1 | 8/2003 | Roltman et al. | |
| 2003/0157587 A1 | 8/2003 | Gomez et al. | |
| 2004/0026250 A1 | 2/2004 | Cummings et al. | |
| 2004/0072242 A1 | 4/2004 | Hunter et al. | |
| 2004/0144735 A1 | 7/2004 | Shepard et al. | |
| 2005/0112572 A1 | 5/2005 | Pincemail et al. | |
| 2005/0118602 A1 | 6/2005 | Li et al. | |
| 2005/0175981 A1 | 8/2005 | Voldman et al. | |
| 2005/0218074 A1 | 10/2005 | Pollock | |
| 2005/0267023 A1 | 12/2005 | Sinclair et al. | |
| 2008/0033258 A1 | 2/2008 | Dudley et al. | |
| 2009/0130706 A1 | 5/2009 | Berzin et al. | |
| 2010/0311087 A1 | 12/2010 | Jensen | |
| 2014/0011185 A1 | 1/2014 | Stroot | |
| 2016/0376650 A1 | 12/2016 | Baranova et al. | |
| 2017/0122954 A1 | 5/2017 | Lebedeva et al. | |
| 2017/0219598 A1 | 8/2017 | Fu et al. | |

OTHER PUBLICATIONS

U.S. Appl. No. 16/002,953, filed Jun. 7, 2018, Methods and Systems for Controlling Oxidative Stress.

Adamczyk et al., The Isotope Array, a New Tool That Employs Substrate-Mediated Labeling of rRNA for Determination of Microbial Community Structure and Function, Appl. And Environ. Microbial., Nov. 2003, vol. 69, No. 11, pp. 6875-6887.

Ahern, Biochemical Reagents Kits Offer Scientist Good Return on Investment, The Scientist, 1995, 9(15): 20.

Al-Qadiri et al., Rapid Detection and Identification of Pseudomonas aeruginosa and *Escherichia coli* as Pure and Mixed Cultures in Bottled Drinking Water Using Fourier Transform Infrared Spectroscopy and Multivariate Analysis, J Agric. Food Chem., 2006, vol. 54, pp. 5749-5754.

Amann et al., Combination of 16s rRNA-Targeted Oligonucleotide Probes with Flow Cytometry for Analyzing Mixed Microbial Populations, Applied & Environ Microbiol (1990) 56(6):1919-1925.

Amann, Fluorescently Labeled, rRNA-Targeted Oligonucleotide Probes in the Study of Microbial Ecology, Mol Ecol (1995) 4:543-554.

Amann et al., Fluorescent-Oligonucleotide Probing of Whole Cells for Determinative, Phylogenetic, and Environmental Studies in Microbiology, J of Bacteriology (1990) 172(2):762-770.

Amann et al., Monitoring the community structure of wastewater treatment plants: a comparison of old and new techniques, REMS Microbiology Ecology, 1998, vol. 25, No. 3, pp. 205-215.

Amann et al. Phylogenetic identification and in situ detection of individual microbial cells without cultivation, Microbial Rev 1995, vol. 59, No. 1, pp. 143-169.

Amann et al., The identification of microorganisms by fluorescence in situ hybridization, Current Opinion in Biotechnology (2001) 12:231-236.

Ashelford et al., PRIMOSE: a computer program for generating and estimating the phylogenetic range of 16S rRNA oligonucleotide probes and primers in conjunction with RDP-II database, Nucleic Acids Research, 2002, vol. 30, No. 15, pp. 3481-3489.

Aßmus et al., Improved in situ tracking of rhizosphere bacteria using dual staining with fluorescence-labeled antibodies and rRNA-targeted oligonucleotides, Microb Ecol, 1997, vol. 33, pp. 32-40.

Baumgärtner et al., Evaluation of Different Fixatives and Treatments for Immunohistochemical Demonstration of coxiella burnetii in Paraffin-Embedded Tissues, J Clin Microbiol (1988) 26(10):2044-2047.

(56) References Cited

OTHER PUBLICATIONS

Bisha et al., Flow-through Imaging Cytometry for Characterization of Salmonella Subpopulations in Alfalfa Sprouts, a Complex Food System, Biotechnol J (2009) 4:880-887.

Bisha et al., Simple Adhesive-Tape Sampling of Tomato Surfaces Combined with RapidFluorescence in situ Hybridization for *Salmonella* Detection, Appl & Environ Microbiol (2009) 75(5):1450-1455.

Bottari et al., "Application of FISH technology for microbiological analysis: current state and prospects" Appl. Microbial. Biotechnol., 2006, vol. 73, pp. 485-494.

Byong-Hee et al., Stimulating Accumulation of Nitrifying Bacteria in Porous Carrier by Addition of Inorganic Carbon in a Coninuous-Flow Fluidized Bed Wastewater Treatment Reactor, J. Biosci Bioeng, 2000, vol. 89, No. 4, pp. 334-339.

Cangelosi et al., Detection of Stable Pre-rRNA in Toxigenic *Pseudonitzschia* Species, Applied and Environmental Microbiology, Dec. 1997, vol. 63, No. 12, pp. 4859-4865.

Cangelosi et al., Depletion of Pre-16S rRNA in Starved *Escherichia coli* Cells, J. of Bacteriology, Jul. 1997, vol. 179, No. 14., pp. 4457-4463.

Coskuner et al., In situ characterization of nitrifiers in an activated sludge plant: detection of *Nitrobacter* Spp, Journal of Applied Microbiology 2002, vol. 93, No. 3, pp. 431-437.

Cox et al., Assessment of Fixatives, Fixation, and Tissue Processing on Morphology and RNA Integrity, Experim & Molecular Path (2006) 80:183-191.

Cox, Quantitative relationships for specific growth rates and macromolecular compositions of *Mycobacterium tuberculosis*, Streptomyces coelicolor A3(2) and *Escherichia coli* B/R: and integrative theoretical approach, Microbiology, 2004, vol. 150, pp. 1413-1426.

Dagley et al., Physciochemical Aspects of Bacterial Growth, Part II. Quantitative Dependence of the Growth Rate of Bact. Lactis Aerogenes on the Carbon Dioxide Content of the Gas Atmosphere, J. Chem. Soc., 1938, pp. 1936-1942.

Dalms et al., Daime, a Novel Image Analysis Program for Microbial Ecology and Biofilm Research, Environ Microbiol (2006) 8(2):200-213.

DuPont, et al., FISH-RiboSyn: A Rapid Approach for Determining the Specific Growth Rate of a Distinct Microbial Population in a Mixed Culture, World Env & Water Res Cong (2007) Restoring Our Natural Habitat, pp. 1-9.

Fuchs et al., Flow Cytometric Analysis of the in situ Accessibility of Escherichia coli 16s rRNA for Fluorescently Labeled Oligonucleotide Probes, Appl & Environ Microbiol, (1998) 64(12):4973-4982.

Hartmann et al., Rapid Identification of *Staphylococcus aureus* in Blood Cultures by a Combination of Fluorescence in situ Hybridization Using Peptide Nucleic Acid Probes and Flow Cytometry, J Clin Microbiol (2005) 43(9):4855-4857.

International Search Report and Written Opinion in Application No. PCT/US2013/048127 dated Nov. 29, 2013, in 22 pages.

Juretschko et al.m Combined molecular and conventional analyses of nitrifying bacterium diversity in activated sludge: Nitrosococcus mobilis and Nitrospira-like bacteria as dominant populations, Appl Environ Microbiol 1998, vol. 64, No. 8, pp. 3042-3051.

Kempf et al., Fluorescent in situ Hybridization Allows Rapid Identification of Microorganisms in Blood Cultures, J Clin Microbiol (2002) 38(2):830-838.

Kerkhof et al., Comparison of Nucleic Acid Hybridization and Fluorometry for Measurement of the Relationship between RNA/DNA Ratio and Growth Rate in a Marine Bacterium, Applied and Environmental Microbiology, May 1993, vol. 59, No. 5, pp. 1303-1309.

Kinsbursky et al., CO2-Nitrification Relationships in Closed Soil Incubation Vessels, Soil Biol Biochem, 1990, vol. 22, No. 4, pp. 571-572.

Kostic et al., A microbial diagnostic microarray technique for the sensitive detection and identification of pathogenic bacteria in a background of nonpathogensm, Analytical Biochemistry, 2007, vol. 360, pp. 244-254.

Leach et al., Same-Day Detection of *Escherichia coli* O157:H7 from Spinach by Using Electrochemiluminescent and Cytometric Bead Array Biosensors, Appl & Environ Microbiol (2010) 76(24):8044-8052.

Li et al., Improved Microscopic Identification of *Clavibacter michiganensis* subsp. *Sepedonicus* Cells by Combining in situ Hybridization with Immunofluorescence, Letters in Appl Microbiol (1997) 24:431-434.

Lim et al., Current and Developing Technologies for Monitoring Agents of Bioterrorism and Biowarfare, Clin Microbiol Reviews (2005) 18(4):583-607.

Lin et al., Using a Resequencing Microarray as a Multiple Respiratory Pathogen Detection Assay, Journal of Clinical Microbiology, Feb. 2007, vol. 45, No. 2, pp. 443-452.

Loy et al., probeBase: an on line resource for rRNA-targeted oligonucleotide probes, Nucleic Acids Research, 2003, vol. 31, No. 1, pp. 514-516.

Manz et al., Abundance and spatial organization of Gram-negative sulfate-reducing bacteria in activated sludge investigated by in situ probing with specific 16S rRNA targeted oligonucleotides, FEMS Microbiology Ecology 25,1998, pp. 43-61.

Mateus et al., An Alternative Approach to Aminodiols from Baylis-Hillman Adducts. Stereoselective Synthesis of Chloramphenicol, Fluoramphenicol and Thiamphenicol, Journal of the Mexican Chemical Society, 2005, vol. 16, No. 3A, pp. 148-158.

Melcer et al., Methods of Wastewater Characterization in Activated Sludge Modeling, Water Environment Research Foundation, 2003, IWA Publishing, Report, #99-WWF-3.

Metcalf et al., Wastewater Engineering Treatment and Reuse, 2003, McGraw-Hill, New York, New York.

Michelinaki et al., Aminoacyl and Peptidyl Analogs of Chloramphenicol as Slow-Binding Inhibitors of Ribosomal Peptidyltransferese: A New Approach for Evaluating Their Potency, Molecular Pharmacology, 1997, 51:139-146.

Mobarry et al., Phylogenetic probes for analyzing abundance and spatial organization of nitrifying bacteria, Appl Environ Microbiol, 1996, vol. 62, No. 6, pp. 2156-2162.

Molin et al., Application of molecular tools for in situ monitoring of bacterial growth activity, Environmental Microbiology, 2003, vol. 1, No. 5, pp. 383-391.

Morris, Investigation of the Optimal Dissolved Co2 Concentration and Ph Combination for Growth of Nitrifying Bacteria (2011, University of South Florida Scholar Commons, Theses and Dissertation, Paper 3256, http//scholarcommons.usf.edu/etd/3256.

Neilsen et al., Studies on the in situ physiology of Thiothrix ssp. present in activated sludge, Environ Microbiol, 2000, vol. 2, No. 4, pp. 389-398.

Noordhoek et al., Sensitivity and Specificy of PCR for Detection of *Mycobacterium tuberculosis:* a Blind Comparison Study among Seven Laboratories, Journal of Clinical Microbiology, 1994, vol. 32, pp. 277-284.

Noutsopoulos et al., The effect of reactor configuration and operational mode on Microthrix parvicella bulking and foaming in nutrient removal activated sludge systems, Water Sci Technol, vol. 46, No. 1-2, pp. 61-64.

Odintsova, Chemolithoautotrophic growth of Thiothrix ramosa, Arch Microbiol, 1993, vol. 160, pp. 152-157.

Oerther et al., Monitoring precursor 16S rRNAs of *Acinetobacter* spp. in activated sludge wastewater treatment systems, Appl & Environ Microbiol, 2000, vol. 66, No. 5, pp. 2154-2165.

Oerther et al., Simultaneous oligonucleotide probe hybridization and immunostaining for in situ detection of *gordona* species in activated sludge, FEMS Microbiol Ecol (1999) 29:129-136.

Oskowis, Re: Numeric Nutrient Criteria Cost Implications for Florida POTW's to G. C. Crist, 2009.

Ouverney et al., Combined Microautoradiography-16S rRNA Probe Technique for Determination of Radioisotope Uptake by Specific Microbial Cell Types In Situ, Applied and Environmental Microbiology, Apr. 1999, vol. 65, No. 4., pp. 1746-1752.

(56) References Cited

OTHER PUBLICATIONS

Peters et al., Rapid Identification of Pathogens in Blood Cultures with a Modified Fluorescence in situ Hybridization Assay, J Clin Microbiol (2006) 44(11):4186-4188.

Pitt et al., Causes and control of Nocardia in activated sludge, 1990, Research Journal WPCF, vol. 64, No. 2, pp. 143-150.

Poulsen et al., Use of rRNA Fluorescence in situ Hybridization for Measuring the Activity of Single Cells in Young and Established Biofilms, Appl Environ Microbiol, 1993, vol. 59, No. 5, pp. 1354-1360.

Purkhold et al., Phylogeny of all recognized species of ammonia oxidizers based on comparative 16S rRNA and amoA sequence analysis: implications for molecular diversity surveys, Appl Environ Microbiol, 2000, vol. 66, No. 12, pp. 5368-5382.

Sakairi et al., Nitrogen Removal in Seawater Using Nitrifying and Denitrifying Bacteria Immobilized in Porous Cellulose Carrier, Wat. Sci. Tech. 1996, vol. 34, No. 7-8, pp. 267-274.

Schloss et al., Quantifying Bacterial Population Dynamics in Compost Using 16S rRNA Gene Probes, Appl. Microbial. Biotechnol., 2005, vol. 66, pp. 457-463.

Schmidt et al. New concepts of microbial treatment processes for the nitrogen removal in wastewater, FEMS Microbiology Reviews 27, 2003, pp. 481-492.

Schramm et al., Identification and Activities In Situ of *Nitrosospira* and *Nitrospira* spp. As Dominant Populations in a Nitrifying Fluidized Bed Reactor, Appl. Environ. Microbial., 1998, vol. 64, No. 9, pp. 3480-3485.

Shibutani et al., Methacarn Fixation: A Novel Tool for Analysis of Gene Expressions in Paraffin-Embedded Tissue Specimens, Lab Invest, 80(2):199-208.

Simpson-Stroot et al., Monitoring Biosensor Capture Efficiencies: Development of a Model Using GFP-Expressing *Escherichia coli* O157:H7, J Microbiol Meth (2008) 72:29-37.

Srinivasan et al., Effect of Fixatives and Tissue Processing on the Content and Integrity of Nucleic Acids, Am J Path (2002) 161(6):1961-1971.

Starks et al., Use of a marker plasmid to examine differential rates of growth and death between clinical and environmental strains of Vibrio vulnificus in experimentally infected mice, Molecular Microbiology, 2006, vol. 61, No. 2, pp. 310-323.

*Staphylococcus aureus* subsp. *aureus* N315 16S ribosomal RNA, complete sequence. Datasheet [online]. National Center for Biotechnology Information, Jan. 31, 2013 [retrieved on Jul. 13, 2014]. Retrieved from the Internet: http://www.ncbi.nlm.nih.gov/nuccore/NR_075000.

Stroot, Novel transcription method confirms growth inhibition of bacteria exposed to domestic wastewater, Ph.D. Dissertation, University of Cincinnati, 2004.

Stroot et al., Elevated Precursor 16S rRNA levels Suggest the Presence of Growth Inhibitors in Wastewater, Water Sci. Technol, 2003, vol. 47, No. 11, pp. 241-250.

Tomlins et al., Precursor Ribosomal Ribonucleic Acid and Ribosome Accumulation in VivoDuring the Recovery of *Salmonella typhimurium* from Thermal Injury, J. Bacterial., 1971, vol. 107, No. 1, pp. 134-142.

Van Dongen et al., The SHARON(R)—Anammox(R) Proces for Treatment of Ammonium Rich Wastewater, Water Science and Technology, 2001, vol. 44, No. 1, pp. 153-160.

Van Hulle et al., Influence of Temperature and pH on the Kinetics of the SHARON Nitration Process, Journal of Chemical Technology and Biotechnology, 2007, vol. 82, No. 5, pp. 471-480.

Van Loosdrecht et al., Upgrading of Wastewater Treatment Processes for Integrated Nutrient Removal—The BCFS® Process, Wat Sci Tech, 1998, vol. 37, No. 9, pp. 209-217.

Vazquez-Paden et al., Applications of Anammox Based Processes to Treat Anaerobic Digester Supernatant at Room Temperature, Bioresource Technology, 2009, vol. 100, pp. 2988-2994.

Vince et al., Choramphenicol and Puromycin, Antimicrobial Agents and Chemotherapy, 1975, vol. 8, No. 4, pp. 439-443.

Wagner et al., In situ analysis of nitrifying bacteria in sewage treatment plants, Water Science & Tech (1996) vol. 34, No. 1-2, pp. 237-244.

Wallner et al., Optimizing Fluorescent in situ Hybridization with rRNA-Targeted Oligonucleotide Probes for flow Cytometric Identification of Microorganisms, Cytometry (1993) 14:136-143.

Wallner et al., Flow Sorting of Microorganisms for Molecular Analysis, Appl & Environ Microbiol (1997) 63(11):4223-4231.

Wellinghausen et al., Rapid Detection of *brucella* spp. In Blood Cultures by Fluorescence in situ Hybridization, J Clin Microbil (2006) 44(5):1828-1830.

Wett et al., The role of Inorganic Carbon Limitation in Biological Nitrogen Removal of Extremely Ammonia Concentrated Wastewater, Water Research, 2003, vol. 37, pp. 1100-1110.

Wett et al., Carbonate addition—an effective remedy against poor activated sludge settling properties and alkalinity conditions in small wastewater treatment plants, Walter Sci Technol, 2003, vol. 48, No. 11-12, pp. 411-417.

Woese et al., Phylogenetic structure of the prokaryotic domain: The primary kingdoms, Proc. Natl. Acad. Sci. USA, Nov. 1977, vol. 74, No. 11, pp. 5088-5090.

Woese et al., Toward a Natural System of Organisms: Proposal for the Domains Archaea, Bacteria, and Eucarya, Proc. Natl. Acad. Sci. USA, Jun. 1990, pp. 4576-4579, vol. 87, No. 12.

Yang et al., Specific Detection of *Dehalococcoides* Species by Fluorescence In Situ Hybridization with 16S rRNA-Targeted Oligonucleotide Probes Applied and Environmental Microbiology, May 2003, vol. 69, No. 5, pp. 2879-2883.

Yu et al., Flow Control Valves for Analytical Microfluidic Chips without Mechanical Parts Based on Thermally Responsive Monolithic Polymers, Analytical Chemistry, 2003, vol. 75, No. 8, pp. 1958-1961.

\* cited by examiner

METHODS AND SYSTEMS FOR CONTROLLING OXIDATIVE STRESS

CROSS-REFERENCE TO RELATED APPLICATIONS

This application is a continuation application of U.S. patent application Ser. No. 16/002,953 filed Jun. 7, 2018, which is a continuation application of U.S. patent application Ser. No. 14/929,124 filed Oct. 30, 2015, which claims the priority benefit under 35 U.S.C. § 119(e) of U.S. Provisional Application No. 62/073,876 filed Oct. 31, 2014. The entireties of all of the foregoing are hereby incorporated by reference herein. Any and all applications identified in a priority claim in the Application Data Sheet, or any correction thereto, are hereby incorporated by reference herein and made a part of the present disclosure.

BACKGROUND

Field

This application relates generally to human health, animal health, biochemical production and/or the like, and more specifically, to methods and systems for measuring and controlling oxidative stress in animals and humans by, inter alia, controlling the percent of blood cells that are induced to produce reactive oxygen species (ROS).

Description of the Related Art

Certain hypotheses suggest that oxidative stress is caused by the consumption of elevated levels of inorganic sulfur. Ultra-exogenous sulfide formation (USF) is caused by the combination of high abundance of sulfate reducing bacteria (SRB) and the consumption of elevated levels of inorganic sulfur. USF results in exposure of blood cells in the right colonic capillary network to elevated sulfide concentration, which induces a reactive oxygen species (ROS) response.

SUMMARY

According to some embodiments, a method for measuring a degree of blood oxidative stress in a subject comprises collecting a first sample of blood from the subject, collecting a second sample of blood from the subject, wherein each of the first and second samples of blood contains plasma, adding a first agent to the second sample, the first agent being configured to induce reactive oxygen species (ROS) in blood cells of the second sample, reacting the second sample after the first agent has been added to the second sample for a first predetermined time period, the first predetermined time period being sufficient to induce production of ROS in blood cells of the second sample, reacting the first sample of blood for the first predetermined time period during a first reacting step, diluting the first and second samples following the reacting steps to reducing a concentration of ROS in the plasma of each of the first and second samples, reacting each of the first and second samples, after dilution, for a second predetermined time period during a second reacting step, isolating the plasma of each of the first and second samples following the second reacting step, adding a second agent to each of the first and second samples following the isolating step, wherein adding the second agent at least partially reacts with ROS present in the plasma of each of the first and second samples, measuring a level in each of the first and second samples indicative of reaction product formed in the plasma after the second agent has reacted with ROS in each of the first and second samples and comparing the level of reaction product of the first sample to the level of reaction product of the second sample, wherein the comparison step is indicative of the degree of blood oxidative stress in a subject.

According to some embodiments, reacting comprises incubation. In some embodiments, the first predetermined time period is equal or greater than the second predetermined time period. In some embodiments, the first predetermined time period is 30 minutes to 2 hours. In one embodiment, the second predetermined time period is 5 to 30 minutes.

According to some embodiments, the isolating step is performed using centrifugation or filtration. In some embodiments, filtration comprises using membrane filtration.

According to some embodiments, the first agent comprises at least one of sodium hydrogen sulfide (NaHS), 4-demethoxydaunorubicin (idarubicin) and tert-Butyl hydroperoxide (TBHP).

According to some embodiments, the second agent comprises a colorimetric dye (e.g., xylenol orange and ferric iron solution, other colorimetric dyes, etc.). In some embodiments, the second agent comprises a fluorescent dye (dihydrodichlorofluorescein, dihydrorhodamine, etc.).

According to some embodiments, the method further comprises providing guidance to the subject for treatment. In some embodiments, the guidance comprises at least one of the following: apheresis, other blood replacement procedures, dietary changes and pharmaceutical correction.

According to some embodiments, the method further comprises treating the subject if the degree of blood oxidative stress is above a threshold or if the degree of blood oxidative stress is indicative of disease. In some embodiments, treating the subject comprises at least one of the following: apheresis, other blood replacement procedures, dietary changes and pharmaceutic correction.

According to some embodiments, a kit for measuring a degree of blood oxidative stress in a subject includes a first agent, and second agent, wherein the first and second agents are used to perform a method as indicated herein.

According to some embodiments, the kit further comprises first and second containers (e.g., vials) for containing the first and second samples of blood, respectively. In some embodiments, the kit further comprises instructions for use, wherein the instructions for use provide instructions to a user in accordance with the steps of the various methods disclosed herein.

According to some embodiments, a method for measuring a degree of small vessel disease in a subject comprises collecting a first sample of arterial blood from the subject, collecting a second sample of venous blood from the subject, wherein each of the first and second samples of blood contains plasma, isolating the plasma of each of the first and second samples, adding a second agent to each of the first and second samples following the isolating step, wherein adding the second agent at least partially reacts with ROS present in the plasma of each of the first and second samples, measuring a level in each of the first and second samples indicative of reaction product formed in the plasma after the second agent has reacted with ROS in each of the first and second samples and comparing the level of reaction product of the first sample to the level of reaction product of the second sample, wherein the comparison step is indicative of the degree of small vessel disease in a subject.

According to some embodiments, the present application describes, inter alia, methods and systems for measuring and controlling oxidative stress in animals and humans. In some embodiments, the degree of oxidative stress can be measured directly by inducing all of the blood cells that are capable of producing excessive reactive oxygen species (ROS) to produce ROS by exposure to an elevated concentration of sulfide and/or other ROS inducing chemicals and measuring the fluorescence intensity of a fluorescent dye that reacts with ROS or color intensity of a dye that reacts with ROS. In some embodiments, a dilution of this sample is used to develop a standard curve that is used to measure the degree of oxidative stress in the original sample. In one embodiment, the plasma ROS concentration is compared in venous and arterial blood samples to evaluate small vessel disease and/or other diseases or indications.

According to some embodiments, oxidative stress is reduced by management of the consumption (e.g., reduction) of inorganic sulfur to meet the daily minimal requirement and/or the consumption of a methanogenic probiotic that reduces the abundance of the sulfate reducing bacteria in the large intestine and associated ultra-exogenous sulfide (USF).

According to some embodiments, oxidative stress is increased by consumption of inorganic sulfur that exceeds the daily minimal requirement by diet or supplementation and/or an intravenous method is used to expose blood cells to an elevated concentration of sulfide or other ROS-inducing chemical that induces the production of reactive oxygen species (ROS).

According to some embodiments, mechanisms involved in USF provide insight into methods for reducing or increasing oxidative stress in animals and humans. In addition, a simple method can be used to measure the percent of ROS-positive blood cells.

According to some embodiments, the ability to induce ROS-positive blood cells can be used in a method for measuring the existing percent of ROS-positive blood cells and for measuring the percent of ROS-positive blood cells after attempts at reducing or increasing oxidative stress. In some embodiments, several methods for reducing oxidative stress are described to reduce ultra-exogenous sulfide formation (USF), one of the primary causes of generating ROS-positive blood cells.

According to some embodiments, a modified diet that meets the minimal daily requirements for inorganic sulfur is managed by the use of a smart phone application and/or some other computing device or system that maintains a daily cumulative measure of the inorganic sulfur consumed by using user input data for the type and amount of food.

According to some embodiments, a methanogenic probiotic may be used to provide a hydrogen competitor for the sulfate reducing bacteria (SRB) in the large intestine. In some embodiments, over time, the methanogenic probiotic can reduce the abundance of the SRB and reduce USF, which can also beneficially allow dietary freedom to consume foods with inorganic sulfur content that exceeds the daily minimal requirement.

According to some embodiments, the increase of oxidative stress may be necessary or helpful to protect animals and humans from catalase-negative pathogens. In some embodiments, a diet with higher levels of inorganic sulfur may promote USF. In some embodiments, a more rapid approach utilizes an intravenous method to expose blood cells to elevated levels of sulfide or ROS inducing chemicals, which are required to induce the ROS response.

According to some embodiments, a test that uses a fluorescent dye that reacts with ROS in the blood is used to estimate the percent of ROS-positive blood cells. In some embodiments, a blood sample could be collected and exposed to an elevated concentration of sulfide or other ROS inducing chemical in order to induce all of the blood cells to produce excessive levels of ROS. In some embodiments, a blood sample with 100% of the blood cells that are ROS-positive can then be used to create a dilution series using either inactivated blood or a suitable diluent, such as saline solution. In some embodiments, a standard curve is generated that relates the whole blood fluorescence to the percent of ROS-positive blood cells. In this way, the percent ROS-positive blood cells can be advantageously evaluated in a step-wise manner to ensure that the human or animal doesn't exceed the targeted percent ROS-positive blood cells.

According to some embodiments, chronic oxidative stress can be reduced to healthier levels by either reducing the daily consumption of inorganic sulfur to just meet the minimal daily requirement or the consumption of a methanogenic probiotic. In some embodiments, in addition to the concern regarding the role of oxidative stress with multiple diseases and cancers, antibiotic resistance in some bacteria has been linked to oxidative stress. In some embodiments, the reduction of oxidative stress in humans or animals suffering from a pathogenic infection may prove to be advantageous for antibiotic therapy. In some embodiments, the reduction of oxidative stress in humans may also be advantageous when evaluating new pharmaceuticals, since excessive ROS may oxidize the pharmaceuticals rendering them non-therapeutic.

According to some embodiments, dietary management of inorganic sulfur is hampered by the lack of food testing data and tools, such as an application for a smart phone application or other "smart" device (e.g., PDA, PC or other computer, etc.). Currently, in some embodiments, the FDA does not require the disclosure of inorganic or organic sulfur content in foods. In some embodiments, inorganic sulfur, such as sulfating agents, is commonly used as a food preservative in the United States and Europe. With food testing data available, the management of USF can become simpler with the use of a smart phone application or the like, which can provide daily cumulative total of consumed inorganic sulfur and guidance for future meals. In some embodiments, an analysis of animal feed consumption may also reveal excessive inorganic sulfur consumption resulting in oxidative stress. In some embodiments, a specially-formulated feed containing lower levels of inorganic sulfur may reduce oxidative stress in animals caused by USF.

According to some embodiments, consumption of a suitable methanogenic probiotic can provide a means for reducing oxidative stress. For example, *Methanobrevibacter* spp. are methanogens that are commonly found in the human gut, but it is absent in individuals that consume elevated levels of inorganic sulfur. In some embodiments, this exclusion is most likely due to *Methanobrevibacter* spp. being catalase-negative, which makes them vulnerable to oxidative stress. In some embodiments, the ideal or preferred methanogenic probiotic would be a catalase-positive *Methanobrevibacter* strain, but higher levels of catalase-negative *Methanobrevibacter* strain may also be effective. In some embodiments, for example, for animals that do not have the option of a modified feed to reduce USF, a methanogen commonly found in the animal gut could be provided as a probiotic.

According to some embodiments, apheresis methods could be used to reduce oxidative stress by the replacement of ROS-positive blood cells with normal blood cells.

According to some embodiments, guidelines for healthy and unhealthy levels of oxidative stress are possible by comparison of percent ROS-positive blood cells to humans with defined health conditions.

According to some embodiments, small vessel disease (SVD) may be detected by comparing the plasma ROS concentration (BlOSvalue) in venous and arterial blood samples.

According to some embodiments, low levels of oxidative stress may be beneficial. In some embodiments, the impact of virulent catalase-negative pathogens, such as *Enterococcus faecium* and Ebola virus, may be reduced by a population, animal or human, that maintains a low level of oxidative stress. In some embodiments, in cases where the consumption of inorganic sulfur meets the minimal daily requirement to maintain health, an increase in the dietary consumption of inorganic sulfur will promote USF. In some embodiments, the consumption of a supplement containing higher levels of sulfate that releases in the large intestine would be a more attractive option when food with higher levels of inorganic sulfur is not available.

According to some embodiments, for the rapid increase of oxidative stress, intravenous (IV) method for exposing blood cells to elevated sulfide, such as NaHS, or other ROS inducing chemicals will induce the ROS response. In some embodiments, in such a method, the percent of ROS-positive blood cells is a function of the percent blood flow and the time. In some embodiments, greater times can result in higher percent ROS-positive blood cells for greater oxidative stress. In some embodiments, for example, for an IV provided to the arm, an assumed blood flow rate of 432 ml/min represents 9% of the cardiac output. In some embodiments, an exposure time of about 2.5 minutes would induce the excessive production of ROS in about 20% of the blood cells.

BRIEF DESCRIPTION OF THE DRAWINGS

These and other features, aspects and advantages of the present inventions are described with reference to drawings of certain preferred embodiments, which are intended to illustrate, but not to limit, the present inventions. It is to be understood that the attached drawings are provided for the purpose of illustrating concepts of the present inventions and may not be to scale.

DETAILED DESCRIPTION

According to some embodiments, mechanisms involved in USF provide insight into methods for reducing or increasing oxidative stress in animals and humans. In addition, a simple method can be used to measure the percent of ROS-positive blood cells.

According to some embodiments, the ability to induce ROS-positive blood cells can be used in a method for measuring the existing percent of ROS-positive blood cells and for measuring the percent of ROS-positive blood cells after attempts at reducing or increasing oxidative stress. In some embodiments, several methods for reducing oxidative stress are described to reduce ultra-exogenous sulfide formation (USF), the primary cause of generating ROS-positive blood cells. In some embodiments, a modified diet that meets the minimal daily requirements for inorganic sulfur is managed by the use of a smart phone application that maintains a daily cumulative measure of the inorganic sulfur consumed by using user input data for the type and amount of food.

According to some embodiments, a methanogenic probiotic may be used to provide a hydrogen competitor for the sulfate reducing bacteria (SRB) in the large intestine. In some embodiments, over time, the methanogenic probiotic will reduce the abundance of the SRB and reduce USF, which can also allow dietary freedom to consume foods with inorganic sulfur content that exceeds the daily minimal requirement. In some embodiments, the increase of oxidative stress may be necessary or helpful to protect animals and humans from catalase-negative pathogens. In some embodiments, a diet with higher levels of inorganic sulfur may promote USF. In some embodiments, a more rapid approach utilizes an intravenous method to expose blood cells to elevated levels of sulfide or other ROS inducing chemicals, which are required to induce the ROS response.

Measurement of Oxidative Stress

Figure 1:
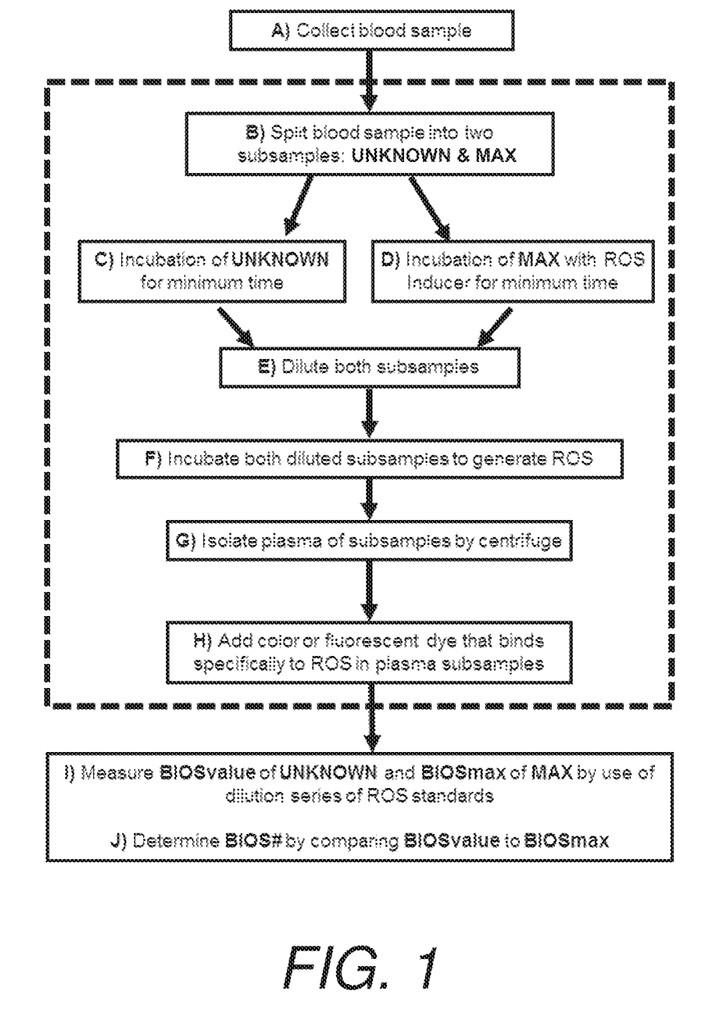
FIG. 1 is a flowchart illustrating a method for determining BlOS for evaluating blood oxidative stress according to one embodiment.

According to some embodiments, a test that uses a fluorescent dye that reacts with ROS in the blood is used to estimate the percent of ROS-positive blood cells. In some embodiment, for example, as illustrated in the flowchart of FIG. 1, a blood sample can be collected using conventional methods (1A). The blood sample is split into two subsamples (1B), referred to as UNKNOWN and MAX in FIG. 1, by transferring equal volumes into new vials used for subsequent centrifugation. Both subsamples can be incubated under temperature and mixing conditions that promote ROS production (1C and 1D), while the MAX subsample includes a ROS inducer.

With continued reference to the embodiment of FIG. 1, after incubation at the minimum time necessary for the ROS inducer to reach maximum rate of ROS production, both subsamples can be diluted (e.g., by 100 fold or more) with a solution (1E) that maintains cell viability. Both diluted subsamples are incubated under conditions that promote ROS production (1F) for a short period (e.g., a few minutes) to generate new ROS that diffuses into the plasma. In some arrangements, following this second incubation step, both subsamples are centrifuged (1G) to separate the plasma from the blood cells. The isolated plasma is transferred to a tube or other container and a ROS-specific dye, fluorescent or color, is added (1H). After sufficient time for the ROS-specific dye to react with the plasma ROS, the ROS concentration in both subsamples (BlOSvalue and BlOSmax) is measured using a fluorimeter or colorimeter by comparing the fluorescent or color intensity to a dilution series using ROS concentration standards (1I).

In some embodiments, the BlOS # is determined by comparing the BlOSvalue of the UNKNOWN subsample to the BlOSmax of the MAX subsample (1J). Alternatively, the MAX subsample could be serially diluted in order to develop an internal standard curve for measuring the relative ROS concentration of UNKNOWN subsample. In some embodiments, a kit (e.g., a commercial test kit) can be used to perform such a test. The various components and steps that can be included in one embodiment of a commercial kit for measuring BlOS # are included within the box defined by the dashed line in FIG. 1. However, additional or fewer components and/or steps can be included in a kit, as desired or required. Accordingly, in some embodiments, the percent ROS-positive blood cells can be advantageously evaluated in a step-wise manner to ensure that the human or animal being evaluated does not exceed the targeted percent ROS-positive blood cells.

Figure 2:
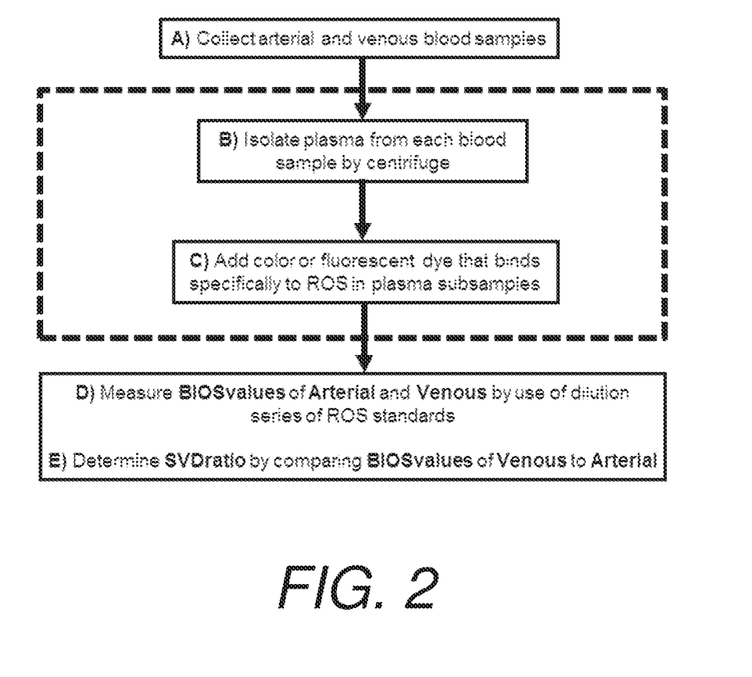
FIG. 2 is a flowchart illustrating a method for determining SVDratio for evaluating small vessel disease according to one embodiment.

According to some embodiments, small vessel disease (SVD) or a similar vascular disorder may be detected by comparing the plasma ROS concentration (e.g., BlOSvalue) in venous and arterial blood samples. As illustrated by the embodiment of FIG. 2, arterial and venous blood samples are collected using conventional methods (2A). Each blood sample can be promptly centrifuged (e.g., immediately after collection) to isolate the plasma, which is transferred to a test tube container (2B). A color or fluorescent dye that reacts specifically to ROS can be added to each subsample (2C). After sufficient time is provided for the dye to react with the ROS in each subsample, BlOSvalues can be measured using a fluorimeter or colorimeter in each subsample by comparison to a standard dilution series of ROS standards (2D). In some arrangements, the SVDratio is determined by comparing the BlOSvalues of the Venous sample to the Arterial Sample (2E).

A kit can be developed in order to determine the SVDratio. In some embodiments, the components and steps of a commercial kit for measuring SVDratio include the various features of the box defined by the dashed line in FIG. 2. However, additional or fewer components and/or steps can be included in a kit, as desired or required. In some embodiments, comparison of the plasma concentration of venous and arterial blood samples may reveal SVD when the ratio (SVDratio) is much greater than 1.5. SVD combined with high percent ROS-positive blood cells can result in acute localized oxidative stress in organs and extremities. In some embodiments, measurement of SVDratio may also be used to monitor the effectiveness of various treatments including, without limitation, diet, exercise, pharmaceuticals and/or the like.

Reduction of Oxidative Stress

According to some embodiments, chronic oxidative stress can be reduced to healthier levels by either reducing the daily consumption of inorganic sulfur to meet the minimal daily requirement or the consumption of a methanogenic probiotic. In some embodiments, in addition to the concern regarding the role of oxidative stress with multiple diseases (e.g., cancers, inflammatory diseases, etc.), antibiotic resistance in some bacteria has been linked to oxidative stress. In some embodiments, the reduction of oxidative stress in humans or animals suffering from a pathogenic infection may prove to be advantageous for antibiotic therapy. In some embodiments, the reduction of oxidative stress in humans may also be advantageous when evaluating new pharmaceuticals, since excessive ROS may oxidize the pharmaceuticals rendering them non-therapeutic.

According to some embodiments, dietary management of inorganic sulfur is hampered by the lack of food testing data and tools. For example, currently, in some embodiments, the FDA does not require the disclosure of inorganic or organic sulfur content in foods. In some embodiments, inorganic sulfur, such as sulfating agents, is commonly used as a food preservative in the United States and Europe. With the necessary food testing data, the management of USF can become simpler. In some embodiments, the use of a smart phone application, other "smart" device (e.g., PDA, PC or other computer, etc.) and/or the like can track and provide daily cumulative total of consumed inorganic sulfur and guidance for future meals to a user. In some embodiments, an analysis of animal feed consumption may also track and reveal excessive inorganic sulfur consumption resulting in oxidative stress. Such tracking can be used to regulate the consumption of inorganic sulfur to desired levels. In some embodiments, a specially-formulated feed containing lower levels of inorganic sulfur can be developed to reduce oxidative stress in animals caused by USF.

According to some embodiments, consumption of a suitable methanogenic probiotic can provide a means for reducing oxidative stress. For example, *Methanobrevibacter* spp. are methanogens that are commonly found in the human gut, but such organisms can be absent in individuals that consume elevated levels of inorganic sulfur. In some embodiments, this exclusion is most likely due to *Methanobrevibacter* spp. being catalase-negative, which makes them vulnerable to oxidative stress. In some embodiments, a specially-designed methanogenic probiotic can be developed. Such a methanogenic probiotic can include a catalase-positive *Methanobrevibacter* strain. In other arrangements, however, higher levels of catalase-negative *Methanobrevibacter* strains can be used to improve the effectiveness of the probiotic, as desired or required. In some embodiments, for example, for animals that do not have the option of a modified feed to reduce USF, a methanogen commonly found in the animal gut could be provided as a probiotic.

According to some embodiments, apheresis methods can be used to replace ROS-positive blood cells with normal blood cells. For example, in some embodiments, blood from the patient and donor can be evaluated to determine the percentage of ROS-positive blood cells by using the methods described herein and/or any other methods. Low oxidative stress blood from the donor can be processed by apheresis methods to isolate healthy white blood cells and platelets. Similarly, high oxidative stress blood from the patient can be processed by apheresis methods that remove the ROS-positive blood cells and use healthy blood cells to replace them.

Figure 3:
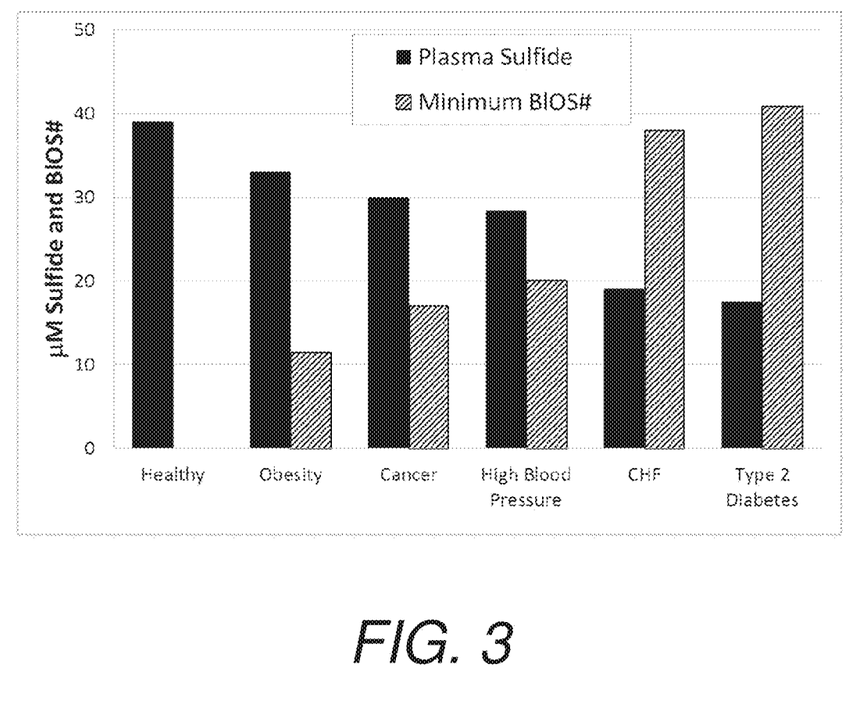
FIG. 3 is one embodiment of a chart generally illustrating a relationship of minimum BlOS # and plasma sulfide concentration for various health conditions.

According to some embodiments, guidelines for healthy and unhealthy levels of oxidative stress can be developed. For example, as illustrated in the embodiment of FIG. 3, such guidelines can be based, at least in part, on a comparison of percent ROS-positive blood cells with defined human health conditions. In some embodiments, a simple linear or other (e.g., non-linear) model can include a constant endogenous sulfide formation rate, plasma sulfide oxidation by the liver, and sulfide oxidation by ROS-positive blood cells.

For example, in some embodiments, healthy individuals exhibit a plasma sulfide concentration of about 39 µM (e.g., 35-45 µM), which corresponds to 0% ROS-positive blood cells. The additional plasma sulfide oxidation by ROS-positive blood cells, measured as BlOS #, can depress the plasma sulfide concentration. In some embodiments, certain health conditions can be observed at maximum plasma sulfide concentrations (and lower), which correspond to a minimum BlOS #, as shown, for example, in FIG. 3. In some embodiments, high blood pressure (or hypertension) is directly linked to depressed plasma sulfide concentration, which relaxes blood vessels at the healthy plasma sulfide concentration. Other health conditions can be linked to chronic or acute inflammation, which, in some instances, may be due to excessive oxidative stress caused by the presence of abnormally elevated levels of ROS-positive blood cells or high BlOS #. Subjects with arthritis can exhibit normal plasma sulfide concentrations due to excessive endogenous sulfide formation, but many also suffer from one or more inflammatory diseases.

According to some embodiments, the measurement of the BlOS # provides an advantage over plasma sulfide, since it can provide guidance on inflammatory diseases for all patients including those suffering from arthritis. The minimum BlOS # corresponding to the onset of arthritis is not shown in FIG. 3, but arthritis is thought to be due to chronic inflammation. In some embodiments, measurement of BlOS # can be advantageous compared to flow cytometry methods. For instance, flow cytometry may not account for the level of ROS production in ROS-positive blood cells. In some embodiments, the BlOS # is a relative measurement of the absolute rate of ROS production of ROS-positive blood cells. It can be a function of both blood cell concentration (WBC and platelets) and the distribution of ROS production of these blood cells. In some cases, the BlOSmax value may exceed the normal limit, which would be indicative of either excessive blood cells or high average rates of ROS production. This high BlOSmax may indicate that the patient is more vulnerable to health conditions normally associated with higher BlOS #. Abnormally high BlOSmax values could be used to adjust the BlOS # value by multiplication with the ratio of measured BlOSmax value to the normal BlOSmax value.

Increase of Oxidative Stress

According to some embodiments, low levels of oxidative stress may be beneficial. In some embodiments, the impact of virulent catalase-negative pathogens, such as *Enterococcus faecium* and Ebola Virus, may be reduced by a population, animal or human, that maintains a low level of oxidative stress. In some embodiments, in cases where the consumption of inorganic sulfur meets the minimal daily requirement to maintain health, an increase in the dietary consumption of inorganic sulfur will promote USF. In some embodiments, the consumption of a supplement containing higher levels of sulfate that releases in the large intestine would be a more attractive option when food with higher levels of inorganic sulfur is not available.

According to some embodiments, for the rapid increase of oxidative stress, intravenous (IV) method for exposing blood cells to elevated sulfide, such as NaHS, or other ROS inducing chemicals will induce the ROS response. In some embodiments, in such a method, the percent of ROS-positive blood cells is a function of the percent blood flow and the time. In some embodiments, greater times can result in higher percent ROS-positive blood cells for greater oxidative stress. In some embodiments, for example, for an IV provided to the arm, an assumed blood flow rate of 432 ml/min represents 9% of the cardiac output. In some embodiments, an exposure time of about 2.5 minutes would induce the excessive production of ROS in about 20% of the blood cells.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely provided as examples and that equivalents of such are known in the art and can be substituted for the reagents explicitly stated herein.

In some embodiments, an application for a smart phone or other computing device (e.g., PDA, tablet, laptop or other computer, etc.) can be used to calculate the daily dietary budget of inorganic sulfur that uses input data from the individual, such as height and weight, and food amount. In one embodiment, a database with inorganic sulfur content of foods would be used to calculate the amount of inorganic sulfur in the food based on the amount of the food. The daily minimal requirement of inorganic sulfur can be calculated for an individual by use of their height and weight. In some embodiments, with complete or substantial information from the user and the foods consumed, the application can provide the daily cumulative total of inorganic sulfur consumed. The application can also provide guidance on foods available at home or at a restaurant that would prevent the individual from exceeding the daily minimal requirement for inorganic sulfur. The application could also store the data for daily inorganic sulfur consumption and health related information related to oxidative stress, such as blood pressure.

In some embodiments, the use of a methanogen probiotic for the control of USF is based on the principle of competitive exclusion. In some embodiments, with USF, the SRB outcompete the methanogens in the gut due to faster specific growth rates for available hydrogen and the oxidative stress sensitivity of the existing methanogens. In order to shift this competition back towards and advantage for the methanogens, a heavy dose of viable methanogens may need to be delivered to the large intestine. In some embodiments, capsules are available that protect bacteria from release in the stomach or small intestine. In some embodiments, an optimal or clinically beneficial dosing of the methanogen probiotic is difficult to without knowledge of the abundance of the SRB and the degree of oxidative stress. In some embodiments, healthy individuals have an upper limit of SRB of about $10^9$/g wet feces with unhealthy individuals harboring $10^{11}$/g wet feces or $5\times10^{12}$ in the right colon. In some embodiments, for a probiotic regimen of $3.6\times10^{11}$ cells/day (e.g., 6 capsules with $60\times10^9$ cells each), a target gut concentration of $10^{12}$ cells in the right colon can be reached in about one week with slower increases thereafter. This calculation assumes a methanogen doubling time of 8 hours, 75% of the right colon contents wasted per day, and about 6 hours of growth per day. However, the above parameter can be modified as desired or required. In some embodiments, such assumptions are adequate to maintain the maximum SRB population with a 5.3 hour doubling time. In some embodiments, a regimen of high methanogen probiotic consumption would be needed initially to overwhelm the SRB. After this initial period of heavy consumption, a lower daily consumption rate may be needed to maintain the methanogen biomass level and prevent appreciable SRB abundance and therefore, USF. In some embodiments, microspheres of freeze-dried methanogen probiotic added to foods offer another approach to increasing the methanogen probiotic effect. In some embodiments, the methanogen probiotic method offers the advantage of minimal or no change in the individual's diet with respect to inorganic sulfur.

In some embodiments, apheresis could be used to replace ROS-positive blood cells with normal blood cells for immediate reduction of oxidative stress. The measurement of the percent ROS-positive blood cells can be used for the evaluation of the donor's and patient's blood prior to apheresis. Evaluation and monitoring of the patient's blood post-apheresis to determine reduction of oxidative stress is also possible with the methods described herein for measuring percent ROS-positive blood cells.

According to some embodiments, the dietary increase of oxidative stress requires knowledge of the inorganic sulfur content of the feed or food for animals or humans, respectively. The daily consumption of inorganic sulfur that exceeds the daily minimal requirement can, in some configurations, promote USF and therefore, oxidative stress. In some embodiments, the degree of oxidative stress is directly related to the level of inorganic sulfur consumed in excess of the daily minimal requirement. In some embodiments, an application (e.g., for a smartphone, tablet, other computing device, etc.) could be used to manage the consumption of inorganic sulfur in order to achieve a target level of oxidative stress.

According to some arrangements, the rapid onset of oxidative stress is possible through the use of IV therapy. A standard IV bag can be used to prepare a 0.9% saline or dextrose solution that also contains a NaHS concentration that delivers the target blood sulfide concentration necessary to induce the ROS response in blood cells. For example, a target blood sulfide concentration of 400 µM would require an IV bag concentration of 2,000 µM, since the IV bag flow rate is about ¼ of the blood flow rate. In some embodiments, for a cardiac output of 4,800 ml/min, the blood flow rate in the arm is 432 ml/min or 9% of the cardiac output. In one embodiment, a total IV bag volume of 270 ml or 2.5 min would induce about 20% of the blood cells to produce high levels of ROS. In some embodiments, if a lower percent of the blood cells is induced to produce ROS due to insufficient contact time or poor mixing, then a larger IV volume can be used to achieve the target percent of ROS-positive cells.

In some embodiments, a method is used to relate the percent of ROS-positive blood cells to the fluorescence intensity of the blood that corresponds to the ROS. In some embodiments, fluorescent dyes are available that react with ROS. With blood collected from the animal or human, a subsample can be exposed to elevated NaHS or other ROS inducing chemical concentration that induces the ROS response. In some embodiments, with sufficient time of no more than one hour, all of the blood cells will be induced to produce ROS. In some embodiments, a fluorescent intensity is measured for this sample that corresponds to 100% ROS-positive blood cells. With a dilution of this sample with inactivated host blood or a suitable diluent, such as saline solution, additional fluorescent intensity measurements can be made in order to develop a standard curve. In some embodiments, with this standard curve, the initial percent of ROS-positive blood cells can be determined.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "collecting," "adding" or "reacting" include "instructing collecting," "instructing adding" or "instructing reacting," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 2 hours" includes "2 hours." Terms or phrases preceded by a term such as "substantially" include the recited term or phrase.

The invention claimed is:

1. A method for determining a degree of a manifestation indicative of disease, disorder or indication in a subject, comprising:
    adding a first agent to a first volume of a blood sample collected from the subject, the first agent being configured to induce a reactive oxygen species (ROS) response in blood cells of the first volume;
    during a first incubation step, incubating: (1) the first volume of blood with the first agent to induce production of ROS in blood cells of the first volume, and (2) a second volume of the blood sample, wherein each of the first and second volumes contains plasma;
    during a dilution step, diluting both a first and second volumes, wherein said diluting is configured to reduce a concentration of ROS in the plasma of each of the first and second volumes;
    during an isolation step, (1) isolating the plasma of the first volume of blood to produce a first volume of plasma, and (2) isolating the plasma of the second volume of blood to produce a second volume of plasma; and
    determining a degree of blood oxidative stress in the subject by comparing the level of ROS response in the first volume and the second volume.

2. The method of claim 1, further comprising a second incubation step, wherein the second incubation step comprises incubating the first volume and the second volume of blood, the second incubation step is performed following the first incubation step.

3. The method of claim 1, further comprising a dilution step, wherein the dilution step comprises diluting both the first volume and the second volume of blood, wherein the diluting is configured to reduce a concentration of ROS in the plasma of each of the first and second volumes of blood.

4. The method of claim 1, further comprising providing guidance to the subject for treatment of the disease, disorder or indication.

5. The method of claim 4, wherein the guidance comprises at least one of the following: apheresis, other blood replacement procedures, dietary changes and pharmaceutical correction.

6. The method of claim 4, wherein the disease, disorder or indication comprises at least one of the following: cancer, inflammatory disease, arthritis, and antibiotic resistance.

7. The method of claim 1, further comprising providing guidance to treat the subject if the degree of blood oxidative stress is above a threshold or if the degree of blood oxidative stress is indicative of the disease, disorder or indication.

8. The method of claim 7, wherein providing guidance to treat the subject comprises guidance related to at least one of the following: an apheresis, a blood replacement procedures, a dietary change, and a pharmaceutical correction.

9. The method of claim 1, wherein the isolation step comprises centrifugation or filtration.

10. The method of claim 1, wherein the first agent comprises at least one of the following: sodium hydrogen sulfide (NaHS), 4-demethoxydaunorubicin (idarubicin), and tert-Butyl hydroperoxide (TBHP).

* * * * *